United States Patent [19]

Luedders et al.

[11] 4,261,982

[45] Apr. 14, 1981

[54] THERAPEUTIC COMPOSITION

[75] Inventors: Wilmer L. Luedders; Richard E. Willins, both of Cincinnati, Ohio

[73] Assignee: The Procter & Gamble Company, Cincinnati, Ohio

[21] Appl. No.: 954,385

[22] Filed: Oct. 25, 1978

Related U.S. Application Data

[63] Continuation-in-part of Ser. No. 850,108, Nov. 19, 1977, abandoned.

[51] Int. Cl.³ .................... A61K 31/71; C07H 17/08
[52] U.S. Cl. ................................ 424/181; 424/180; 536/9
[58] Field of Search .................. 536/9; 424/181, 180, 424/289, 227

[56] References Cited

U.S. PATENT DOCUMENTS

| | | | |
|---|---|---|---|
| 3,969,516 | 7/1976 | Stoughton | 421/181 |
| 4,000,263 | 12/1976 | Hebborn | 536/9 |
| 4,039,681 | 8/1977 | Abdel-Monem | 424/289 |
| 4,063,014 | 12/1977 | Hallas et al. | 536/9 |

FOREIGN PATENT DOCUMENTS 7707785  3/1977  France ........................................ 536/9

OTHER PUBLICATIONS

Unterman, W., et al., Acad. Rep. Populare Romine, Feliala, Iasi Studii / Cercetari Stiimt. /mt , Chim., 13, 59–66, (1962).
Pertsev et al., Farmatsevtichnü Zhurnal, (kiev), 29, No. 2, pp. 42–48, (1974).

*Primary Examiner*—Johnnie R. Brown
*Assistant Examiner*—Blondel Hazel
*Attorney, Agent, or Firm*—Jerry J. Yetter; Steven J. Goldstein; Michael J. Roth

[57] ABSTRACT

Zinc compounds, especially zinc salts of carboxylic acids, react with erythromycin to provide zinc erythromycin. Topical compositions containing zincerythromycin are especially useful as a topical treatment for acne.

14 Claims, No Drawings

THERAPEUTIC COMPOSITION

RELATED APPLICATION

This application is a continuation-in-part of U.S. application, Ser. No. 850,108, filed Nov. 19, 1977 now abandoned.

*Acne vulgaris* and other types of acne and acneiform skin maladies associated with hyperplasia of the sebaceous follicle are often treated by the oral administration of antibiotics. Tetracycline has been the traditional drug of choice, but other antibiotics such as erythromycin, lincomycin and clindamycin have also been prescribed for this use. While oral administration of these drugs often constitutes an effective treatment regimen for acne, oral therapy has several disadvantages. For example, the oral administration of antibiotics subjects the entire body to the antibiotic composition while only the localized acne lesion requires treatment. Moreover, almost all antibiotics have some undesirable side effects when taken orally.

In contrast with oral dosing in the treatment of acne, topical application of antibiotics delivers the antibiotic to the afflicted situs and minimizes the antibiotic levels in the circulatory and gastrointestinal systems. Properly administered, the therapeutic benefit of topical antibiotic therapy in treating skin disorders can be comparable with, or superior to, that achieved by oral antibiotic therapy, while avoiding the undesirable side effects of oral administration.

BACKGROUND ART

Compositions for topical treatment of acne are known. Smith, U.S. Pat. No. 3,952,099, issued Apr. 20, 1976, discloses compositions for treating acne lesions by topical application of tetracycline antibiotics in a skin penetration vehicle comprising sucrose monooleate, decyl methyl sulfoxide and alcohol.

Stoughton, U.S. Pat. No. 3,969,516, issued July 13, 1976, and *Arch. Dermatol.*, 84 182 (1976), discloses a method for topically treating acne by applying formulations containing various antibiotics in N-methyl-2-pyrrolidone. The data presented are said to indicate that tetracycline in a pyrrolidone-based penetrating vehicle does not effectively control the inflammatory lesions of acne. In addition to tetracycline, compositions of erythromycin, erythromycin derivatives and clindamycin in the same vehicle were studied. The combination of erythromycin and N-methyl-2-pyrrolidone reportedly gave results which were better than tetracycline in the same vehicle, whereas the antibiotic lincomycin gave superior results in controlling the inflamed acne lesions.

In light of the foregoing, it is clear that the effectiveness of any particular antibiotic as a topical treatment of acneiform skin diseases can vary, depending on how well the antibiotic composition penetrates through the skin.

It has been suggested in the scientific literature that zinc ions may be implicated in the biochemical changes associated with wound healing in humans or lower animals. Zinc salts of various antibiotic/antimicrobial agents are known: e.g., zinc undecylenate and zinc bacitracin. U.S. Pat. No. 4,039,681, issued Aug. 2, 1977 teaches the use of zinc methionine to treat acne. German Offenlegungsschrift 2517413, 13/11/75, discloses dermatologic agents containing zinc salts or complexes, and the use of such compositions for treating acne or seborrhoea. Other zinc-containing dermatological compositions, primarily based on zinc oxide, are known: U.S. PHARMACOPOEIA XIX; BRITISH PHARMACOPOEIA 1968; Martindale, THE EXTRA PHARMACOPOEIA 26th Ed.

W. D. Unterman and Th. Mironeanu *Acad. Rep. Populare Romine, Filiala, Iasi Studii Cercetari Stiint. Chim.* 13(1): 59–66 (1962), describe the chromatographic and electrochromatographic migration of zinc and other metal cations in the presence of antibiotics, including erythromycin. However, the conjoint use of zinc and erythromycin in the manner of this invention does not seem to have been suggested, heretofore.

By the present invention, novel zinc/erythromycin compositions characterized by enhanced skin penetration properties are provided. The compositions herein are suitable for human and veterinary uses. These compositions are especially useful when applied topically in the treatment of "acne", especially *Acne vulgaris*.

DISCLOSURE OF THE INVENTION

The present invention is based on the discovery that the percutaneous penetration of zinc salts is greatly enhanced in the presence of erythromycin. Accordingly, the compositions herein are especially useful in the topical treatment of disorders of the skin and underlying tissues. While not intending to be limited by theory, it appears that the benefits associated with the topical use of zinc/erythromycin compositions in the manner of the present invention are due to improved delivery of zinc into the skin to the underlying afflicted tissues.

The present invention encompasses mixtures of zinc salts and erythromycin, as well as the reaction product of zinc compounds with erythromycin compounds, said reaction product being referred to hereinafter as "zinc erythromycin".

The present invention also encompasses compositions for topical application to skin in the treatment of skin disorders, comprising:

(1) a minor proportion, i.e., less than 50%, generally from about 0.001% to about 25%, preferably from about 0.5% to about 10%, of an active agent selected from the group consisting of zinc erythromycin and mixtures of zinc compounds and erythromycin compounds; and (2) the balance comprising a pharmaceutically-acceptable topical carrier.

This invention also encompasses methods for treating acne and acneiform skin diseases, as well as other skin disorders and other diseases of bacterial origin, by topically applying compounds and compositions of the foregoing type to the afflicted situs.

The present invention also encompasses methods for promoting wound healing in patients in need of such treatment comprising topically applying compounds and compositions of the foregoing type to the wounded situs.

The zinc compounds are erythromycin compounds employed herein are all toxicologically acceptable for use internally in humans and lower animals. Accordingly, the present invention also encompasses a method for systemically (i.e., as by oral administration or parenteral administration) treating dermatological and systemic diseases and for promoting would healing comprising administering systemically to a patient in need of such treatment a safe and effective amount of zinc erythromycin or a mixture of a zinc compound and an erythromycin compound, all as more fully disclosed hereinafter.

Specifically, this invention relates to zinc-containing erythromycin compositions which are characterized by superior skin and tissue penetrating properties. The compositions herein are especially useful for the topical treatment of *Acne vulgaris* and other skin disorders. The method for treating acne embodied in this invention comprises topically applying a safe and effective amount of the present compositions on the skin of the patient at the afflicted situs.

By "erythromycin" or "erythromycin compound" herein is meant "erythromycin base", which is the antibiotic produced by the strain *Streptomyces erythreus*, erythromycin base in the form of hydrated crystals, as well as other compounds of erythromycin, i.e., the well-known salts of erythromycin base and acids, and the ester derivatives of erythromycin. Non-limiting examples of commercially-available compounds of erythromycin include: erythromycin estolate, which is the lauryl sulfate salt of the propionic acid ester of erythromycin; erythromycin glucoheptonate, which is the glucoheptonic acid salt of erythromycin; erythromycin lactobionate, which is prepared from erythromycin base and lactobiono-δ-lactone; erythromycin propionate, the propionic acid ester of erythromycin; erythromycin stearate, which includes both the stearic acid salt of erythromycin and the stearic acid ester of erythromycin; and erythromycin ethyl succinate, which is the ester of erythromycin and ethyl succinic acid.

By "zinc erythromycin" herein is meant the reaction product of an erythromycin compound, especially erythromycin base, with zinc or zinc compounds, preferably zinc salts, especially the zinc salts of carboxylic acids, e.g., zinc acetate, zinc propionate, zinc valerate, and the like. While not intending to be limited by theory, both polarography and NMR spectrography provide definite evidence of complex formation when erythromycin reacts with zinc salts. NMR results indicate that the binding site between the zinc and the erythromycin is on the vicinal carbons of the glucosamine moiety (—OH and —N(CH$_3$)$_2$) of erythromycin. Polarographic results indicate that the zinc:erythromycin stoichiometry is probably 1:2. In addition, infrared analysis shows small shifts consistent with complex formation, and X-ray crystallography shows a distinct pattern for zinc-erythromycin which differs from patterns for either zinc acetate or erythromycin base.

By "topical application" is meant directly spreading or laying onto epidermal tissue. Topical application can be achieved by rubbing, applicator pads, containers with applicator fitments, or any other convenient means.

By "afflicted situs" is meant areas of the skin which are inflamed, the acne comedones, papules, pustules, and cysts (acne lesions) and the skin immediately surrounding such areas.

By "safe and effective amount" is meant an amount which is effective to alleviate the inflammation and lesions of the acne or acneiform skin diseases and yet causes no undesirable side effects (at a reasonable benefit/risk ratio). For topical application, a dose range of the topical compositions formulated in the manner of this invention of from about 0.01 mg/cm$^2$ per day to about 25 mg/cm$^2$ per day is effective. The dosage can vary with the individual, depending on such factors as the type and severity of the skin disorder, the frequency of application, the area of the body which is afflicted, and like factors within the knowledge of the user or attending physician. The dosage will also vary with the concentration of zinc-plus-erythromycin or zinc erythromycin in the topical composition. Generally, from about 0.001 mg/cm$^2$ to about 12.5 mg/cm$^2$ of the zinc-/erythromycin mixture or zinc erythromycin compound is applied to the afflicted situs once or twice daily to afford relief from acneiform skin afflictions. Similar quantities are useful in the topical treatment of other skin disorders and dermatoses of bacterial origin, e.g., impetigo (*impetigo contagiosa*) or ecthyma; bullous impetigo; scalded skin syndrome (*dermatitis exfoliative*); erysipelas; folliculitis (including furuncles/carbuncles); hidradenitis suppurativa; paronychial infections; erythrasma; and the like. The present compositions afford improved zinc ion delivery into and through human and lower animal tissues and this effect coupled with the potent antimicrobial action of the erythromycin make the compositions especially useful for topical and systemic administration to promote wound healing.

By "comprising" herein is meant that various other compatible ingredients can be present in the present compositions in such proportions as will not adversely affect the stability and penetrating effectiveness of the zinc/erythromycin compositions. The term "comprising" thus encompasses and includes the more restrictive terms "consisting" and "consisting essentially of" within its scope.

All percentages are by weight, unless otherwise specified.

BEST MODE

The ingredients which supply the pharmacologically/antimicrobially-active agents used in the present invention comprise a zinc compound and an erythromycin compound.

The zinc compounds employed herein can be selected from any of the toxicologically-acceptable zinc salts; the zinc salts of carboxylic acids are preferred. Non-limiting examples of typical zinc salts which can be used in the practice of this invention include the zinc salts of C$_1$–C$_{12}$ carboxylic acids and polycarboxylic acids, including zinc acetate, zinc propionate, zinc butyrate, zinc pentanoate, zinc hexanoate, zinc heptanoate, zinc 2-ethyl hexanoate, zinc octanoate, zinc nonanoate, zinc decanoate, zinc undecanoate, and zinc dodecanoate. Other zinc salts useful herein include the zinc salts of amino acids such as zinc alanine, zinc methionine, zinc glycine, zinc asparagine, zinc aspartine, zinc serine, and the like. Other zinc salts useful herein include zinc citrate, zinc maleate, zinc benzoate, zinc acetylacetonate, and the like. Other zinc salts useful here include zinc chloride, zinc sulfate, zinc phosphate, and zinc bromide. The zinc chalcogens can also be used herein, but are not preferred inasmuch as they do not interact rapidly with erythromycin. Likewise, the more acidic zinc salts such as zinc chloride are not preferred for use herein inasmuch as they do not appear to penetrate skin optimally.

Highly preferred for use herein are zinc salts of the shorter-chain (C$_2$–C$_8$) carboxylic acids and zinc acetylacetonate. Especially preferred for use herein are zinc acetate, zinc acetylacetonate, and zinc 2-ethyl hexanoate (known commercially as "zinc octoate").

The foregoing zinc compounds are articles of commerce and are available in either anhydrous or hydrated forms which are suitable for use herein. As with any zinc-containing material intended for use in contact with living tissue, the zinc compounds employed herein should be free from toxicologically-unacceptable traces of heavy metals such as arsenic.

The erythromycin component of the instant compositions can comprise erythromycin "base" or any of the other well-known erythromycin drug materials, especially those disclosed hereinabove.

Preparation of the zinc erythromycin compound in the manner of this invention is achieved by simply admixing a zinc compound of the foregoing type with the erythromycin base in a convenient reaction medium. By "convenient reaction medium" is meant any solid or liquid system in which the zinc or zinc compound and erythromycin or erythromycin compound can be admixed in reactive form. For example, ethanol is a convenient reaction medium for zinc acetate and erythromycin base, even though zinc acetate is only sparingly soluble in ethanol, because the addition of erythromycin immediately draws the zinc acetate into solution as the zinc erythromycin acetate complex. Thus, non-aqueous, polar solvents, e.g., alcohols, especially ethyl alcohol, constitute appropriate reaction media. Alternatively, other convenient reaction media may be selected in which the zinc component and the erythromycin component are both fully soluble, but in which zinc erythromycin is insoluble, allowing the zinc erythromycin complex formed to be separated by precipitation. The zinc erythromycin compound is formed at room temperature, under extremely mild conditions, from a ca. 1:1 mole ratio of zinc salt and erythromycin.

In a typical procedure, an excess of zinc acetate dihydrate and erythromycin base (1:1 mole ratio) are allowed to react in the following manner: the zinc acetate dihydrate particles are suspended in ethyl alcohol, in which they are sparingly soluble; erythromycin base is added to the ethanolic suspension of zinc acetate, which causes the zinc acetate to dissolve, with the resulting formation of a solution of zinc erythromycin.

In a similar procedure, zinc 2-ethyl hexanoate (slight excess) is combined with erythromycin base, at room temperature in diisopropyl sebacate, to provide a zinc erythromycin compound, presumably as the complex zinc di-erythromycin di-2-ethylhexanoate.

In similar fashion are prepared zinc acetylacetonate erythromycin; zinc methionyl erythromycin; zinc citrate erythromycin; zinc alanyl erythromycin; and the like, depending on the choice of zinc compound used as the starting material.

The zinc erythromycin compounds prepared in the foregoing manner can be isolated by removal of the solvent or by precipitation from a reaction medium in which zinc erythromycin is insoluble; alternatively, they can be used in the reaction solvent for treatment of dermatoses, or can be blended with topical carrier materials to provide finished compositions having desirable aesthetic properties.

In an alternative mode, zinc and erythromycin compositions suitable for use as topical medicaments can be prepared by simply blending any of the toxicologically-acceptable zinc compounds, especially those disclosed hereinabove, in a pharmaceutically-acceptable, compatible carrier.

Compatible carriers used with the zinc/erythromycin active ingredients in the topical compositions prepared in the manner of this invention can comprise any cosmetic carrier which does not react with the zinc compounds or with the erythromycin or the zinc erythromycin compound, and which is not irritating or otherwise detrimental to the afflicted situs. In general, any of the common, non-water based cosmetic carriers are useful herein. Typical carriers include short chain alcohols and ketones and emollients such as hydrocarbon oils and waxes, lanolin and lanolin derivatives, silicone oils, monoglyceride, diglyceride, and triglyceride esters, fatty acids, fatty alcohols, alkyl and alkenyl esters of fatty acids, alkyl and alkenyl diesters of dicarboxylic acids, polyhydric alcohols and their ether and ester derivatives; wax esters, and beeswax derivatives. Preferred carriers contain materials which enhance the delivery of erythromycin through skin. These include the alkyl and alkenyl esters of fatty acids, such as isopropyl myristate; alkyl and alkenyl diesters of dicarboxylic acids, such as diisopropyl sebacate; fatty alcohols such as lauryl alcohol; and ester derivatives of polyhydric alcohols, such as propylene glycol dipelargonate. Such carriers generally will comprise from 51% to 99.999% of the topical compositions.

Optional components at levels of from about 0.01% to about 25% of the topical compositions can be used to provide aesthetic benefits thereto. Such optional components include common thickening agents, such as cross-linked polymethylene polymers, various gums, microcrystalline waxes, polyethylene glycols, and trace amounts of fragrance materials, coloring agents, and the like.

It has been determined that the storage stability of the present compositions is adversely affected by the presence of water. Accordingly, the compositions herein are preferably water-free, i.e., contain less than about 1% water.

Thus, preferred topical compositions herein are homogeneous mixtures which consist essentially of from about 0.3% to about 5% of an active agent selected from the group consisting of: (1) 1:10 to 10:1 (wt.) mixtures of erythromycin compound and either zinc acetate, zinc 2-ethyl hexanoate, or zinc acetylacetonate; and (2) the reaction product (ca. 1:2 mole basis) of either zinc acetate, zinc 2-ethyl hexanoate, or zinc acetylacetonate and erythromycin base; the balance of the topical composition comprising a substantially water-free cosmetic carrier.

Because it has also been determined that the storage stability of the present compositions is adversely affected by the presence of ethanol unless the compositions are refrigerated, the compositions herein are preferably ethanol-free, i.e., contain less than about 1% ethanol. Accordingly, highly preferred topical compositions herein are storage-stable homogeneous mixtures which comprise from about 0.3% to about 5% of an active agent selected from the group consisting of: 1:10 to 10:1 (wt.) mixtures of erythromycin compound and either zinc acetate, zinc 2-ethyl hexanoate, or zinc acetylacetonate; or the reaction product (ca. 1:2 mole basis) of either zinc acetate, zinc 2-ethyl hexanoate, or zinc acetylacetonate and erythromycin base; and the balance of the topical composition comprising a substantially water-free, substantially ethanol-free carrier.

Topical treatment regimens according to the practice of this invention comprise applying the compositions herein directly to the skin at the situs of the dermatosis. The rate of application and duration of treatment will, of course, depend on the severity of the condition, the response of the particular patient, and related factors within the sound medical judgment of an attending physician or the patient. In general, for the compositions within the compositional ranges noted above, application rates of from about 0.01 mg/cm² to about 25 mg/cm² of afflicted situs per day are used. Application can be made once, or preferably several times, daily for periods of a week or more, to relieve dermatoses and to promote wound healing.

INDUSTRIAL APPLICABILITY

The following example illustrates a preferred topical composition prepared and used in the manner of this invention, but is not intended to be limiting thereof.

EXAMPLE I

| Ingredient | Percent (wt.) |
| --- | --- |
| Erythromycin base | 2.3 |
| Zinc acetate . 2H₂O | 0.7 |
| Polyethylene-vinyl acetate copolymer | 10.0 |
| Polydimethylsiloxane | 51.9 |
| Diisopropyl sebacate | 20.0 |
| Stearyl alcohol | 15.0 |
| Menthol | 0.1 |

The above ingredients are mechanically blended at 80°–90° C. (to liquefy the polyethylene-vinyl acetate copolymer) and cooled with agitation to provide a semi-solid gel composition adapted for topical application to skin.

A person afflicted with acne lesions is treated by topically applying the composition of Example I to the acne lesions at a rate of 0.5 mg/cm² of composition twice a day to reduce the number of acne lesions and attendant inflammation.

Erythromycin ethylsuccinate is substituted for the erythromycin base of Example I and similar results are obtained.

The zinc acetate dihydrate of Example I is replaced by an equivalent amount of zinc octanoate, zinc butyrate, zinc acetylacetonate, zinc methionate and zinc hexanoate, respectively, and equivalent results are secured.

The composition of Example I is applied three times daily (3.0 mg/cm²) for a period of two weeks in the management of impetigo.

EXAMPLE II

| Ingredient | Percent (wt.) |
| --- | --- |
| Zinc erythromycin* | 4.0 |
| Ethanol | 64.8 |
| Diisopropyl sebacate | Balance |

*Prepared by reacting a mixture (1:1 mole) of zinc 2-ethyl hexanoate and erythromycin base in ethanol in the manner disclosed herein.

The composition of Example II is an emollient formulation requiring refrigeration for long-term stability, and is applied topically to skin. The zinc erythromycin in this composition penetrates into and through human skin and provides an excellent topical treatment for acne when used regularly, per the treatment regimen of Example I.

When isopropyl myristate is substituted for an equivalent amount of the diisopropyl sebacate in the composition of Example II, equivalent results are secured.

The composition of Example II is modified by replacing the reaction product of zinc 2-ethyl hexanoate and erythromycin base with the reaction product of erythromycin base and the following zinc compounds, respectively: zinc alanine; zinc methionine; zinc acetylacetonate; zinc citrate, zinc ascorbate; zinc undecylenate; and zinc glycine and excellent acne remedies are secured in each instance.

EXAMPLE III

| Ingredient | Percent (wt.) |
| --- | --- |
| Erythromycin base | 4 |
| Zinc acetylacetonate | 4 |
| Polydimethylsiloxane | 40 |
| Isopropyl myristate | Balance |

The above ingredients are mechanically blended and a fluid product which is suitable for enhancing the penetration of zinc and erythromycin into and through animal tissue is provided. The composition is applied topically twice daily in the treatment of acne, folliculitis, ecthyma, and like skin disorders of bacterial origin.

In the composition of Example III, the erythromycin base is replaced by an equivalent amount of erythromycin propionate and erythromycin stearate, respectively, and equivalent results are secured.

EXAMPLE IV

| Ingredient | Percent (wt.) |
| --- | --- |
| Erythromycin base | 6 |
| Zinc acetylacetonate | 7 |
| Cetyl alcohol | 15 |
| Isopropyl alcohol | 25 |
| Isopropyl myristate | Balance |

The erythromycin base and zinc acetylacetonate are blended in ethanol to provide zinc erythromycin (acetylacetonate). The ethanol is removed and the remaining ingredients are added and a fluid product which is characterized by enhanced penetration of erythromycin and zinc into and through animal tissue is secured. The composition is topically applied (0.05–5 mg/cm²) twice daily directly to acne lesions to reduce inflammation and pustules.

The composition of Example IV is applied topically to open wounds to prevent bacterial contamination and promote healing. A fast-acting anesthetic such as benzocaine can be added to the composition to lessen pain when the composition is applied to open wounds.

The foregoing compositions which comprise the zinc/erythromycin materials are useful in the practice of the present invention by virtue of their ability to penetrate into and through epidermal tissue to the underlying situs of bacterial infection in the treatment of a wide variety of dermatoses. It is to be understood that finished, aesthetically pleasing formulations are not necessary for this use and that simple solutions of zinc/erythromycin in ethanol solvent can also be used for such purposes, but such solutions are not preferred because of their need for refrigeration and reduced penetration.

The systemic administration of antibiotics for the treatment of acne and acneiform skin disorders and to combat bacterial infestation during wound healing processes is a well-known medical treatment. By the present invention, zinc compounds in combination with erythromycin compounds, as disclosed hereinabove, or zinc erythromycin, can be systemically administered to a patient in need of such treatment. For oral administration, it is preferred that non-emetic zinc compounds be used. Zinc oxide is useful in this regard. In the stomach, zinc oxide dissolves to provide a systemically-available source of zinc ions.

Accordingly, the present invention provides compositions and methods for systemically treating acne and acneiform skin disorders and for promoting wound healing. Such methods comprise administering systemically to a patient in need of such treatment a safe and effective amount of zinc erythromycin or a mixture of a zinc compound and an erythromycin compound. For oral administration, an amount of an erythromycin compound in the range from about 50 mg to about 3000 mg per patient/day is typically employed. The amount of zinc compound can range from about 5 mg to about 2000 mg per patient/day. If a zinc erythromycin compound of the type disclosed herein is used systemically, from about 50 mg to about 3000 mg per patient/day is employed. Of course, the amount used in any given situation will depend on the age and general health of the patient, the type of disorder being treated, the weight of the patient, and like factors within the knowledge of the attending physician.

The following examples illustrate typical compositions of the present type which are especially useful for systemic administration, but are not intended to be limiting thereof.

EXAMPLE V

An ethanol solution suitable for oral administration is as follows.

| Ingredient | Percent (wt.) |
| --- | --- |
| Zinc erythromycin* | 10.0 |
| Ethanol | 90.0 |

*Prepared by heating a 1:1 mole mixture of zinc acetate and erythromycin base in the manner disclosed herein.

The composition of Example V is administered orally (10 ml, twice daily) to a human patient as a treatment for acne and acneiform skin disorders. The composition is used in similar fashion to promote wound healing.

Refrigeration is necessary for long-term stability.

EXAMPLE VI

An alcoholic suspension of zinc acetate containing dissolved zinc erythromycin adapted for oral administration is as follows.

| Ingredient | Percent (wt.) |
| --- | --- |
| Zinc erythromycin* | 2.0 |
| Zinc acetate | 10.0 |
| Ethanol | Balance |

*Prepared per Example V

The composition of Example VI is administered orally (10 ml, twice daily) to a human or lower animal to combat bacterial infection and to provide an excess of zinc ion to promote wound healing.

Refrigeration is necessary for long-term stability.

What is claimed is:

1. A process for preparing zinc erythromycin by admixing a zinc compound soluble in said admixture selected from toxicologically-acceptable zinc salts of carboxylic acids and amino acids with erythromycin base in a solid or liquid reaction medium wherein said zinc compound and erythromycin base can be admixed in reactive form.

2. A process according to claim 1 wherein the reaction medium is ethanol.

3. A process according to claim 1 wherein the zinc compound is a salt of a $C_2$-$C_8$ carboxylic acid.

4. A process according to claim 1 for preparing zinc erythromycin comprising admixing erythromycin base with a zinc compound selected from zinc acetate, zinc 2-ethyl hexanoate and zinc acetylacetonate in ethanol.

5. A composition for topical application to skin in the treatment of skin disorders and dermatoses of bacterial origin, comprising:
   (1) a minor proportion of a mixture of zinc compounds soluble in said composition, selected from toxicologically-acceptable zinc salts of $C_1$-$C_{12}$ carboxylic acids, zinc salts of amino acids, zinc acetylacetonate, zinc chloride, zinc bromide, zinc citrate, zinc maleate, zinc benzoate, zinc phosphate, zinc sulfate, or mixtures thereof, together with erythromycin compounds, selected from erythromycin base, erythromycin estolate, erythromycin glucoheptonate, erythromycin lactobionate, erythromycin propionate, erythromycin stearate, erythromycin ethyl succinate, and mixtures thereof, wherein the ratio of zinc compound to erythromycin compound is from about 1:10 to about 10:1; and
   (2) the balance comprising a pharmaceutically-acceptable topical carrier.

6. A composition according to claim 5 which is substantially water-free.

7. A composition according to claim 6 which is substantially ethanol free.

8. A composition according to claim 6 which comprises from about 0.001% to about 25% by weight of the active agent.

9. A composition according to claim 5 wherein the zinc compound is selected from zinc acetate, zinc 2-ethyl hexanoate and zinc acetylacetonate.

10. A method for treating skin disorders and dermatoses of bacterial origin comprising applying topically thereto at an afflicted situs a safe and effective amount of the composition of claim 9.

11. A method for treating skin disorders and dermatoses of bacterial origin comprising applying topically thereto at an afflicted situs a safe and effective amount of the composition of claim 7.

12. A method for promoting wound healing comprising topically applying a safe and effective amount of zinc erythromycin to the afflicted situs.

13. A method for systemically treating skin disorders and dermatoses of bacterial origin and systemic bacterial infections and for promoting wound healing comprising administering systemically to a patient in need of such treatment a safe and effective amount of zinc erythromycin or a mixture of a zinc compound selected from toxicologically-acceptable zinc salts and an erythromycin compound selected from erythromycin base, salts of erythromycin base with acids, and ester derivatives of erythromycin.

14. A method for treating acne comprising applying topically at an afflicted situs a safe and effective amount of the composition of claim 6.

* * * * *